(12) United States Patent
Cavazza et al.

(10) Patent No.: US 6,610,699 B2
(45) Date of Patent: Aug. 26, 2003

(54) USE OF L-CARNITINE AND ITS ALKANOYL DERIVATIVES IN THE PREPARATION OF MEDICAMENTS WITH ANTICANCER ACTIVITY

(75) Inventors: Claudio Cavazza, Rome (IT); Claudio Pisano, Aprilia (IT); Loredana Vesci, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/769,488

(22) Filed: Jan. 26, 2001

(65) Prior Publication Data

US 2001/0044465 A1 Nov. 22, 2001

Related U.S. Application Data

(63) Continuation of application No. PCT/IT99/00242, filed on Jul. 27, 1999.

(30) Foreign Application Priority Data

Jul. 30, 1998 (IT) .......................................... RM98A0511
Apr. 7, 1999 (IT) .......................................... RM99A0206

(51) Int. Cl.[7] ...................... A61K 31/44; A61K 31/335; A61K 31/28; A61K 31/195
(52) U.S. Cl. ...................... 514/283; 514/449; 514/492; 514/561
(58) Field of Search .............................. 514/561, 449, 514/492, 283

(56) References Cited

FOREIGN PATENT DOCUMENTS

| WO | 96 15810 | 5/1996 |
|---|---|---|
| WO | 96 19243 | 6/1996 |
| WO | 96 36348 | 11/1996 |
| WO | 97 05862 | 2/1997 |
| WO | 97 34596 | 9/1997 |

OTHER PUBLICATIONS

Vermorken et al., Semin. Oncol. (1995), 22(4, Suppl. 8), 16–22 Abstract Only.*

Kuzmits et al., Blut. (1986) 53 (3), 132 Abstract Only.*

Kuzmits Biological Abstracts, vol. BR32, No. 136210, 1987 Abstract No. 136210 L–carnitine supplementation decreases chemotherapy–induced catabolism in testicular cancer XP002128878 & Annual Meeting of the Austrian Society of Hematology and Oncology vol. 53, No. 3, 1986, p. 132.

* cited by examiner

*Primary Examiner*—Jerome D. Goldberg
(74) *Attorney, Agent, or Firm*—Nixon & Vanderhye

(57) ABSTRACT

Alkanoyl L-carnitines of the formula:

(I)

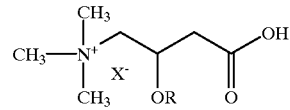

where R is hydrogen or a $C_{2-8}$ alkanoyl group and $X^-$ is an anion of a pharmaceutically acceptable salt, are used in conjunction with anticancer agents such as taxol or bleomycin to improve the therapeutic index and reduce side effects typical of anticancer chemotherapy.

8 Claims, No Drawings

USE OF L-CARNITINE AND ITS ALKANOYL DERIVATIVES IN THE PREPARATION OF MEDICAMENTS WITH ANTICANCER ACTIVITY

This is a continuation of PCT application PCT/IT99/00242, filed Jul. 27, 1999, the entire content of which is hereby incorporated by reference in this application.

The invention described herein relates to the use of L-carnitine and alkanoyl L-carnitines in the preparation of medicaments useful in the treatment of tumours, particularly in combination with anticancer agents for the treatment of tumours.

BACKGROUND TO THE INVENTION

It is well-known that the use of anticancer agents in human therapy causes a large number of toxic or side effects which may be life-threatening for the patients. These complications, in fact, may lead to a reduction in the doses of the agents, and occasionally to discontinuation of the therapy itself.

Reduction of the dose or discontinuation of the therapy in many cases causes a deterioration of the individual's general condition because it favours the development of relapses, with consequences which are sometimes fatal for the patient.

Another very important and strongly felt aspect in the hospital setting and among the families of oncological patients is the concept of "improving the quality of life" of the patients under treatment.

It is equally well known that patients undergoing regular polychemotherapy for cancer are subject to a substantial weight loss.

The growing number and importance of the anticancer agents used in human therapy, the main limitation of which continues to be the occurrence of toxic or side effects, mean that this problem is still a matter for considerable concern.

Thus, the discovery of new agents or new, appropriate combinations of different agents capable of substantially reducing the toxic or side effects caused by anticancer agents used in human therapy is much to be desired.

Previous uses of L-carnitine in combination with anticancer agents are already known.

In experimental animal models, it has been demonstrated that rats treated with doxorubicin alone show a greater weight loss than a group of rats treated with the same substance in combination with L-carnitine (Senekowitsch R, Lohninger A, Kriegel H., Staniek H., Krieglsteiner H. P., Kaiser E. Protective effects of carnitine on adriamycin toxicity to heart. In: Kaiser E., Lohninger A., (eds.). Carnitine: its role in lung and heart disorders: 126–137. Karger, Basel-New York, 1987).

U.S. Pat. No. 4,713,370 describes the use of carnitine in combination with cytostatic agents such as daunomycin, N-acetyl-daunomycin and daunomycin oxime to reduce the cardiac toxicity of these compounds. U.S. Pat. No. 4,267,163 describes the use of carnitine in combination with cytostatic agents such as adriamycin, adriamycin-14-octanoate, 4'-epi-adriamycin, adriamycin beta-anomer and 4'-epi-adriamycin gamma-anomer to reduce the cardiac toxicity of these compounds. U.S. Pat. No. 4,751,242 describes the use of acetyl L-carnitine for the therapeutic treatment of peripheral neuropathies.

Other studies have addressed the evaluation of the protective effects of carnitines on anthracycline-induced cardiac toxicity (Neri B., Comparini T., Milani A., Torcia M., Clin. Trial J. 20, 98–103, 1983; De Leonardis V., De Scaizi M., Neri B., et al. Int. J. Clin. Pharm. Res. 70, 307–311, 1987).

The patent and bibliographical references cited above demonstrate that many efforts have been made in an attempt to reduce the toxic or side effects of anticancer agents, without, however, solving this serious problem in a satisfactory manner.

Carboplatin is a structural analogue of cisplatin and its associated nephrotoxicity, though by no means negligible, is less than that of cisplatin.

Vincristine is a well-known anticancer agent which has toxic effects, particularly at the level of the immune system.

Taxol is a natural extract, first isolated from the bark of *Taxus breuifolia*, with anticancer properties and has proved neurotoxic and myelotoxic in human subjects. It is used for the treatment of tumours resistant to platinum therapy, but gives rise to greater cumulative toxicity in the peripheral nervous system. It has also been ascertained that taxol induces neutropenia in the subjects treated (Rowinsky e al.; Semin. Oncol. (Aug. 20, 1993 (4 suppl 3), 1–15; Onetto e al. J. Natl. Cancer Inst. Monogr. (1993); (15):131–9).

Bleomycin is typically used in young patients with testicular cancer, lymphoma, and other types of tumours. The pulmonary toxicity of bleomycin is characterised by destruction of the alveolar epithelial barrier and the consequent intra-alveolar proliferation of fibroblasts and deposition of extracellular matrix components (Karam H et al.; Cell Biol. Toxicol (1998 Feb);14(1):13–22). Type 2 pneumocytes are not capable of regenerating the damaged or lost epithelium.

One of the general problems of pharmacological therapy is the therapeutic index of the agents, that is to say the ratio of the therapeutically effective dose to the toxic dose, or, at any rate, the dose that gives rise to the onset of side effects.

The medical community still perceives the need for therapeutic regimens which allow the patient to face up to the treatment, which, in the case of anticancer chemotherapy is particularly hard to support, while at the same time conserving an acceptable quality of life. These considerations also apply to the therapeutic treatment of animals, for instance, so-called pets.

The natural tendency to reduce the doses, and thus the use of pharmaceutical forms suitable for therapeutically useful administrations without obliging the patient to take the agents too often, contrasts with the minimum effective doses typical of each anticancer agent.

SUMMARY OF THE INVENTION

Surprisingly, it has been found that the co-ordinated use—this term will be precisely defined below—of an anticancer agent and L-carnitine or an alkanoyl L-carnitine, as defined below, exerts an unexpected synergistic effect on the activity of the anticancer agent.

In the context of the invention described herein, it has also been found, in an entirely unexpected way, that the co-ordinated use of a therapeutically effective amount of an anticancer agent, in particular taxol, carboplatin, bleomycin and vincristine, and a detoxifying amount of L-carnitine or of an alkanoyl L-carnitine, in which the linear or branched alkanoyl has 2–8 carbon atoms, or one its pharmacologically acceptable salts, affords a potent protective effect against the toxicity and side effects of the anticancer agent, without impairing its efficacy, thus giving rise, amongst other things, to a substantial improvement in the quality of life and a prolonging of life itself in the subjects treated, whether human subjects or animals.

It has also been found that said coordinated use has an inhibitory effect on tumour metastases.

Therefore one object of the invention described herein is the use the compound of formula (I):

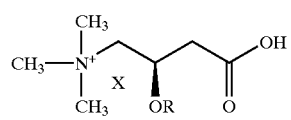

where R is hydrogen or an alkanoyl group with 2 to 8 carbon atoms, and $X^-$ represents the anion of a pharmaceutically acceptable salt, for the preparation of a medicament comprising an anticancer agent, characterised in that said compound produces an synergistic effect on the activity of the anticancer agent.

Also an object of the invention described herein is the co-ordinated use the compound of formula (I) according to which the side effects of the anticancer agent in said medicament are substantially reduced.

A further object of the invention described herein is the use the compound of formula (I) in the preparation of a medicament useful for inhibiting metastases.

Yet another object of the invention described herein are combinations the compound of formula (I) with anticancer agents and the related pharmaceutical compositions.

The well known lack of toxic or side effects of alkanoyl L-carnitines makes the use of these compounds particularly safe even for long periods of treatment, for the prevention or treatment of toxic or side effects, such as weight loss, heart, kidney and central nervous system damage, peripheral nervous system damage, particularly neuropathy or neutropenia caused by taxol, or lung damage induced by bleomycin.

The implementation of the invention described herein also contributes to improving the quality of life of the patients treated; one need only think of the physical suffering caused by peripheral neuropathy, neutropenia, respiratory complications or debilitation due to weight loss caused by these agents.

These and other objects of the invention described herein will be described in detail in the embodiment forms of the invention, also by means of examples.

In the context of the invention described herein, the terms "antineoplastic", "anticancer" and "antiproliferative" are to be understood as being essentially synonymous.

DETAILED DESCRIPTION OF THE INVENTION

In the context of the invention described herein, what is meant by "coordinated use" of the aforesaid compounds is, indifferently, either (i) co-administration, i.e. the substantially simultaneous or sequential administration of L-carnitine or an alkanoyl L-carnitines or one of its pharmacologically acceptable salts and of an anticancer agent, or (ii) the administration of a composition comprising the aforesaid active ingredients in combination and in a mixture, in addition to optional pharmaceutically acceptable excipients and/or vehicles.

The invention described herein thus covers both the co-administration of L-carnitine or an alkanoyl L-carnitine or one of its pharmacologically acceptable salts of formula (I) and of the anticancer agent, and pharmaceutical compositions, which can be administered orally, parenterally or nasally, including controlled-release forms, comprising the two active ingredients in a mixture. Preferably, the alkanoyl L-carnitine is selected from the group consisting of acetyl L-carnitine (hereinafter abbreviated to ALC or Alcar), propionyl L-carnitine (hereinafter abbreviated to PLC), butyryl L-carnitine, valeryl L-carnitine and isovaleryl L-carnitine, or one of their pharmacologically acceptable salts. The ones preferred are acetyl L-carnitine, propionyl L-carnitine and butyryl L-carnitine.

Though clear from the following detailed description of the invention, one can also envisage the co-ordinated use of an anticancer agent, such as taxol, acetyl L-carnitine and propionyl L-carnitine, or of bleomycin and acetyl L-carnitine, or—a further possibility—of acetyl L-carnitine and taxol or carboplatin or vincristine. In all these embodiments, L-carnitine can be used in the co-ordinated use.

Co-administration also means a package, or manufactured article, comprising distinct administration forms of L-carnitine or one of the aforesaid alkanoyl L-carnitines, or one of their pharmacologically acceptable salts and of an anticancer agent, accompanied by instructions for the coordinated simultaneous or time-scheduled intake of the active ingredients according to a dosage regimen established by the primary care physician, on the basis of the patient's condition.

What is meant by a pharmacologically acceptable salt of L-carnitine or of an alkanoyl L-carnitine is any salt of the latter with an acid that does not give rise to toxic or side effects. These acids are well known to pharmacologists and to experts in pharmaceutical technology.

Examples of pharmacologically acceptable salts of L-carnitine or of the alkanoyl L-carnitines, though not exclusively these, are chloride; bromide; iodide; aspartate; acid aspartate; citrate; acid citrate; tartrate; acid tartrate; phosphate; acid phosphate; fumarate; acid fumarate; glycerophosphate; glucose phosphate; lactate; maleate; acid maleate; mucate; orotate, oxalate; acid oxalate; sulphate; acid sulphate; trichloroacetate; trifluoroacetate; methane sulphonate; pamoate and acid pamoate.

One preferred form of daily dosing of L-carnitine or alkanoyl L-carnitine for clinical use is a composition comprising an amount of L-carnitine or an alkanoyl L-carnitine, preferably acetyl or propionyl L-carnitine, equivalent to 0.1 to 3 g, and preferably 0.5 to 3 g.

The invention described herein is advantageous in the prevention or treatment of toxic or side effects such as weight loss, heart, kidney and central nervous system damage, peripheral nervous system damage, peripheral neuropathy and particularly the myelosuppression and lung damage caused by the above-mentioned anticancer agents.

What is meant by substantially protective effect is the prevention, reduction or elimination of the side effect to a statistically significant extent.

The embodiment of the invention described herein also contributes to healing and to prolonging the lives of the patients thanks to the increase in therapeutic success due to the possibility of maintaining the scheduled treatment protocols or of increasing the doses of the chemotherapeutic agent, without having to discontinue the treatment due to contraindications.

A further benefit which is obtained with the invention described herein is related to the quality of life of the subjects treated; in fact, as already mentioned, the elimination or reduction of the physical suffering caused by a peripheral neuropathy or by debilitation due to weight loss favours the patient's ability to be self-sufficient. From the economic standpoint, there are obvious savings in terms of the costs borne by hospital facilities or by the families for the patient's care.

Myelosuppression is one of the toxic side effects that may manifest themselves as a result of administration of taxol, a chemotherapeutic agent used in the therapy of various tumours, for example, of the breast, ovaries, lungs (small cell and otherwise), head and neck (Slichenmeyer and Von Hoff: J. Clin. Pharmacol. (1990), 30, 770–778). The vehicle adopted for taxol, also in the commercial pharmaceutical forms (TAXOL®, Bristol Myers Squibb), is a derivative of polyethoxylated castor oil, known commercially as Cremophor® EL and is capable of inducing histamine release and anaphylactoid reactions in the dog and in human subjects (Slichenmeyer and Von Hoff: ibid; Bury et al.: Allergy (1992), 47, 624–629; Hershkoviz et al.: J. Leukoc. Biol. (1994), 56, 495–501; Inokuma et al.: J. Vet. Med. Sci. (1994), 56, 45–49). In view of the fact that the marketed drug is vehicled in Cremophor® EL, the problem of the myelotoxicity relating to the preparation used in therapy has been tackled.

One of the most serious problems encountered in the course of proliferative diseases is the metastatic spread of the tumour, which sometimes advances to such an extent as to render useless the treatment of the primary tumour and itself becomes the cause of death.

In a first preferred embodiment of the invention described herein, L-carnitine, combined with an anticancer agent such as taxol, carboplatin or vincristine, ensures an extension of survival of the subject treated.

In a second embodiment of the invention described herein, acetyl L-carnitine has shown an unexpected degree of protective activity against taxol-induced side effects, such as peripheral neuropathy, myelosuppression and weight loss.

In a third embodiment of the invention described herein, acetyl L-carnitine has shown surprising antimetastatic activity when administered concomitantly with taxol, particularly in lung cancer.

According to another preferred embodiment of the invention described herein, propionyl L-carnitine has shown an unexpected synergistic effect in combination with taxol.

It has been found that taxol induces severe neutropenia with a nadir after the 3rd–4th injection of the compound.

When ALC is used according to the invention described herein, no adverse effects on the anticancer action of the drug are found.

ALC can be conveniently administered orally, without, for that reason, excluding other administration routes which an expert in the field may deem it advisable to adopt, particularly, by injection, to be administered concomitantly, for example, in the same infusion vial, with the anticancer agent, or in sequence, as established by the expert in the field.

Equally, propionyl L-carnitine (PLC) has shown a synergistic effect with the therapeutic activity of taxol.

It is therefore evidently advantageous to provide a ternary combination, also in separate dosage forms, or in some way combined, of acetyl L-carnitine as a protective agent, propionyl L-carnitine as a synergistic agent and taxol. This combination also comprises other anticancer agents which show a synergistic effect or induce substantially reduced side effects as a result of the combination according to the invention described herein. It may also be advantageous to add L-carnitine to the above-mentioned combination.

One specific object of the invention described herein is a pharmaceutical composition comprising a therapeutically effective amount of taxol together with a protective amount of acetyl L-carnitine and a synergistic amount of propionyl L-carnitine, in a mixture with pharmaceutically acceptable vehicles and/or excipients.

In a different embodiment, it is in any case advantageous to provide a binary combination of acetyl L-carnitine, as a protective agent, and bleomycin.

As regards those aspects relating to industrial applicability, the invention described herein also provides, in one of its possible embodiments, for a kit containing a) a pharmaceutical composition comprising a therapeutically effective amount of an anticancer agent; b) a pharmaceutical composition comprising at least one alkanoyl L-carnitine, as defined above, in an amount suitable for producing a synergistic effect with said anticancer agent; c) a pharmaceutical combination comprising at least one alkanoyl L-carnitine and/or L-carnitine, as defined above, in an amount suitable for producing a substantially protective action against the side effects of said anticancer agent. The kit according to the invention described herein may also be presented in the form of a) a pharmaceutical composition comprising a therapeutically effective amount of an anticancer agent; b) a pharmaceutical composition comprising at least one alkanoyl L-carnitine in an amount suitable for producing a synergistic effect with said anticancer agent. Alternatively, the kit according to the invention described herein may also be presented in the form of a) a pharmaceutical composition comprising a therapeutically effective amount of an anticancer agent; and b) a pharmaceutical composition comprising at least one alkanoyl L-carnitine and/or L-carnitine in an amount suitable for producing a substantially protective action against the side effects of said anticancer agent.

Specific examples of the above-mentioned kits refer to carboplatin, vincristine, taxol and bleomycin as the anticancer agents.

We shall now describe the ways of implementing the invention described herein with reference to the preferred embodiment, using taxol as the anticancer agent, acetyl L-carnitine as the substantially protective agent and propionyl L-carnitine as the substantially synergistic agent.

It remains understood that the expert in the field may complete the experimental protocols with his or her own general knowledge of the field in which he or she operates, possibly resorting to neighbouring sectors in case of need.

We report here below the results of the most significant experiments suitable for demonstrating the unexpected and surprising protective effect obtained by the combination of L-carnitine or its derivatives with the above-mentioned anticancer agents.

EXAMPLE 1

Variations in Survival Time in Rats Treated with Anticancer Agents

The purpose of this experiment is to demonstrate and evaluate the protective effect expressed as an increase in survival time, induced by L-carnitine in a murine experimental model.

Groups of 10 male Wistar rats aged 3 months (Charles River) were used, housed at 22±2° C., with 50±15% relative humidity and a 12 hour light/darkness cycle, maintained with water and feed "ad libitum".

The substances used were: L-carnitine, taxol, carboplatin, and vincristine.

The rats were treated with the anticancer agents intravenously (i.v.) at the doses corresponding to their respective $LD_{30}$, $LD_{50}$ and $LD_{80}$.

The treatments with L-carnitine, 200 mg/kg, were administered subcutaneously once daily, starting 8 days prior to administration of the anticancer agent and continuing for another 14 days.

The mortality of the rats, identified immediately prior to treatment by means of progressive numbers on their tails, was monitored daily for 14 days after administration of the anticancer agent; the experimental data were evaluated using the Wilcoxon and Log-Rank tests and the statistical significance obtained in the evaluation of the experimental data is reported in Table 1 here below.

TABLE 1

Evaluation of survival time of rats treated with L-carnitine and anticancer agent at three different dosage levels.

| Compound | AMOUNT OF ANTICANCER AGENT ADMINISTERED CORRESPONDING TO: | | |
|---|---|---|---|
|  | $LD_{80}$ (high dose) | $LD_{50}$ (medium dose) | $LD_{30}$ (low dose) |
| Carboplatin + L-carnitine | P < 0.05 (p < 0.08) | P < 0.01 (p < 0.06) | P < 0.43 (p < 0.54) |
| Taxol + L-carnitine | P < 0.02 (p < 0.05) | P < 0.51 (p < 0.42) | P < 0.15 (p < 0.15) |
| Vincristine + L-carnitine | P < 0.08 (p < 0.04) | P < 0.02 (p < 0.l2) | P < 0.49 (p < 0.73) |

The significance refers to the combination versus the respective control (anticancer agent alone at the same dose)

The results obtained, reported in Table 1, show a significant lengthening of survival time in the groups treated with L-carnitine and anticancer agent.

The results of the statistical analysis reported in Table 1 show two "p" values. The first was calculated using the Wilcoxon test; the second, i.e. the "p" value in brackets, was calculated using the Log-Rank test.

The discrepancies between the results of the two tests, the Wilcoxon and the Log-Rank test, are due to the fact that the former is more powerful in detecting differences in the first part of the survival curve, and the latter in the second part.

In the experiment performed, the differences in survival times occur mainly in the first part of the curve.

The lack of statistical significance in the comparisons between the lower doses may be explained by the fact that, owing to the low number of deaths, the tests are not very powerful in detecting differences between groups.

EXAMPLE 2

Protective Effect of Acetyl L-carnitine on an Experimental Model of Taxol-induced Peripheral Neuropathy The purpose of this study is to demonstrate and evaluate the protective properties of acetyl L-carnitine administered one week prior to taxol at two different doses of the latter (16 mg/kg and 8 mg/kg), by measuring the sensory nerve conduction velocity (SNCV), determined on the tail and by means of the H reflex.

Female Wistar rats aged 3 months (Charles River) were used, housed at 22±2° C., with 50±15% relative humidity and a 12 hour light/darkness cycle.

The rats were identified immediately prior to treatment by means of progressive numbers on their tails and were maintained with water and feed "ad libitum".

The substances used were acetyl L-carnitine and taxol.

The following experimental groups were formed:
1. Controls.
2. Sham (group receiving taxol solution solvent).
3. Taxol 16 mg/kg.
4. Acetyl L-carnitine+taxol 16 mg/kg.
5. Taxol 8 mg/kg.
6. Acetyl L-carnitine+taxol 8 mg/kg.

The following treatment schedule was used: the Sham animals received taxol solution solvent (cremophor/ethanol) intraperitoneally (i.p.); taxol was administered i.p. once a week for 5 weeks; the treatments with L-carnitine, 200 mg/kg, were administered orally (os) once daily via a gastric tube, starting one week prior to the first taxol administration and continuing for another 4 weeks (5 weeks in all).

The following method was used: the animals, anaesthetised with a gaseous mixture composed of 0.45 halothane, nitrogen protoxide and oxygen, were depilated in the stimulation zone and placed on an operating table. The recordings and stimulations of the sensory responses were done using an Ote Biomedica Phasis II electromyograph. In view of reports in the literature of nerve conduction velocity depending on the animal's body temperature, it was necessary to keep the latter constant throughout the experiment, measuring it with a rectal probe, with the aid of a BM 70002-type thermoregulator for animals (Biomedica Mangoni).

Measurement of the sensory fibre conduction velocity was obtained on the tail with steel ring-type stimulation and measurement electrodes, 46 cm in length (Modelec digital ring electrodes), using a stimulation intensity equal to the threshold value with a duration of 100 microseconds.

The mean value of 300 responses was taken as potential.

The sensory nerve conduction velocity, expressed in ms, was calculated as the ratio of the distance between the two stimulation points, expressed in mm, to the difference in latency of the waves produced by proximal (the nearest) and distal (the farthest from the dorsal spine) stimulation, expressed in ms.

The velocity was measured in all groups of animals both in basal conditions (prior to any administration) and after 5 weeks of treatment.

The results were expressed as means±standard deviation; significance was assessed using the "t"-test, for both independent and paired data, with a statistical significance cut-off of p<0.05.

The sensory nerve conduction velocity data measured on the caudal nerve are given in the Table 2 here below.

TABLE 2

Taxol-induced neuropathy: sensory nerve conduction velocity (m/s) measured on the animals' tails in basal conditions and after treatment with L-carnitine.

| TREATMENT | MEASUREMENTS | | % vs CONTROL | % vs TAXOL |
|---|---|---|---|---|
|  | BASAL | 5 WEEKS |  |  |
| Control | 29.5 ± 0.8 (6) | 41.0 ± 0.8 Δ (6) | — | — |
| Sham | 30.0 ± 0.8 (8) | 41.0 ± 0.3 Δ (6) |  |  |
| Taxol 16 mg/kg | 30.2 ± 0.9 (6) | 34.0 ± 1.1**Δ (6) | −17 ± 0.03 |  |

TABLE 2-continued

Taxol-induced neuropathy: sensory nerve conduction velocity (m/s) measured on the animals' tails in basal conditions and after treatment with L-carnitine.

| TREATMENT | MEASUREMENTS | | % vs CONTROL | % vs TAXOL |
|---|---|---|---|---|
| | BASAL | 5 WEEKS | | |
| Acetyl L-carnitine + Taxol 16 mg | 30.0 ± 1.4 (6) | 37.1 ± 1.8**ΔÅ (6) | | 9 ± 0.02 |
| Taxol 8 mg/kg | 30.0 ± 0.7 (8) | 37.5 ± 0.4**Δ (8) | −9 ± 0.04 | |
| Acetyl L-carnitine + Taxol 8 mg | 30.2 ± 1.2 (8) | 39.4 ± 0.6**ΔÅ (8) | | 5 ± 0.02 |

Values are means ± standard deviation.
In brackets the number of animals used.
t-test (independent data) ** = p < 0.01 vs CONTR.; ▲ = P < 0.01 vs corresponding taxol.
t-test (paired data) Δ = p < 0.01 vs basal.

In basal conditions, all the groups of animals present well-matched nerve conduction values.

The measurement at 5 weeks reveals a statistically significant increase (p<0.01) in sensory nerve conduction velocity in all groups compared to basal conditions.

Treatment with the taxol solvent (Sham group) did not modify nerve conduction velocity values as compared to the control group. The administration of taxol induced a significant reduction (P<0.01) in sensory nerve conduction velocity compared to the control group; this reduction was dose-dependent: −17% with the 16 mg/kg dose and −9% with the 8 mg/kg dose.

Treatment with acetyl L-carnitine induced a statistically significant increase (p<0.01) in sensory nerve conduction velocity in both groups; 9% compared to the 16 mg/kg taxol group and 5% compared to the 8 mg/kg taxol group.

On the basis of the results obtained it will be noted that acetyl L-carnitine is capable of affording statistically significant protection against taxol-induced neurotoxicity.

EXAMPLE 3

Protective Effect of Acetyl L-carnitine on Taxol-induced Weight Loss

The animals used in the preceding experimental model were weighed prior to starting treatment (basal values) and at the end of treatment.

The data given in Table 3 here below demonstrate the substantial and unexpected protective effect exerted by acetyl L-carnitine on loss of body weight caused by taxol treatment.

TABLE 3

Body weight of animals treated with taxol alone or in combination with acetyl L-carnitine.

| TREATMENT | MEASUREMENTS | | % vs BASALE | % vs SHAM |
|---|---|---|---|---|
| | BASAL | 5 WEEKS | | |
| Control | 209 ± 9.1 (6) | 250 ± 12.4 (6) | +20* | |
| Sham | 205 ± 12.2 (8) | 234 ± 12.8 (8) | +14* | |
| Taxol 8 mg/kg | 210 ± 9.1 (8) | 237 ± 20.8 (8) | +13** | +1 |
| Taxol 16 mg/kg | 212 ± 12.5 (6) | 180 ± 16.0 (6) | −15** | −23● |
| Alcar + Taxol 8 mg/kg | 207 ± 6.7 (8) | 228 ± 20.5 (8) | +10*** | −2 |
| Alcar + Taxol 16 mg | 210 ± 6.5 (6) | 216 ± 37.6 (6) | +3 | −8 |

Values are means ± standard deviation.
In brackets the number of animals used.
t-test (independent data) ● = p < 0.001 vs sham.
t-test (paired data) *p < 0.001; p < 0.01; *p < 0.05 vs basal.

EXAMPLE 4

Protective Effect of Acetyl L-carnitine on Taxol-induced Neutropenia

It has been ascertained by the inventors of the invention described herein that the neutropenic effect of taxol reaches a nadir after the 3rd–4th injection.

To evaluate the action of ALC in combination with taxol, both on the quantity of circulating neutrophils and on tumour growth, the degree of ALC-induced protection both on treatment with taxol alone and in animals inoculated with a murine cancer of the breast (L-MM3) was assessed, and tumour growth was evaluated in animals treated with ALC and taxol or with ALC alone. Taxol treatment caused a significant reduction in polymorphonucleates. Oral administration of acetyl L-carnitine combined with taxol treatment proved capable of significantly preventing the reduction in neutrophil granulocytes induced by the anticancer agent. As regards tumour growth, taxol, when injected according to the same schedule used for the evaluation of neutrophil granulocytes, was found to significantly inhibit the growth of L-MM3, which was monitored until the tumour reached approximately 2 cm in size. Combined treatment with taxol and ALC for 14 days did not affect the anticancer action of taxol.

In conclusion, in this tumour model, too, taxol caused severe neutropenia and ALC, administered continuously over the period in which this type of bone marrow toxicity occurs, was capable of preventing the taxol-induced reduction in polymorphonucleates. At the same time, the action of ALC did not affect the anticancer activity of taxol.

EXAMPLE 5

Effect of Administration of Acetyl L-carnitine (ALC) in Combination with Taxol i.p. on Neutropenia in the Mouse In a study conducted according to Good Laboratory Practice (GLP), to evaluate the action of acetyl L-carnitine (ALC) in combination with taxol on taxol-induced neutropenia, the animals were treated both with ALC plus taxol, and with taxol or ALC alone. In this model, the amount of circulating neutrophils was measured.

Taxol was found to induce a significant reduction in neutrophil granulocytes within only 6 hours of the third injection, and thus severe neutropenia occurs with a nadir after the 3rd–4th injection.

Acetyl L-carnitine inner salt (sterile ampoule), solubilised in water for injectable preparations, was used. Each ampoule of ALC is dissolved in 4 ml of water for injections (Solution O). Two ml of (O) are brought up to 25 ml with sterile PBS (Sigma), so as to have 10 mg/ml for subcutaneous administration (100 mg/kg/ 10 ml); 0.8 ml of (O) are brought to 50 ml with PBS in order to have 2 mg/ml for oral administration (100 mg/kg/50 ml).

Taxol (paclitaxel (INDENA)) is weighed, solubilised in the previously prepared specific vehicle (Cremophor® EL (BASF), diluted 1:1 with ethanol) and stored at +4° C. sheltered from the light. At the time of use, the 12 mg/ml solution is diluted 1:4 with saline in phosphate buffer (PBS) (SIGMA,) and injected i.p. (30 mg/kg/10 ml).

The essential experimental indications are given here below:

Animals: female BALB/c mice weighing 18–20 g (Harlan) Animal house conditions: 4–5 mice per cage; temperature 22±2° C.; relative humidity 55±15%; air changes 15–20/h; 12 h light/darkness cycle (7.00 a.m.–7.00 p.m. light); makrolon cages (26.7×20.7×14 cm) with stainless steel grilled covers; dedusted, sterile, corn-cob shaving litters.

Diet: 4RF21 feed (company: Mucedola), food and water available "ad libitum".

The randomisation is casual in blocks of animals, i.e. the animal house attendant transfers the mice from the boxes to the cages, completing one cage at a time. In a second phase, the attendant provisionally identifies all the mice, weighs them, and, if the weights present significant differences between groups, moves the animals from one cage to another, keeping the number of animals per cage unchanged, so as to have well-matched overall weights between one cage and another. Each cage is labelled with a card bearing the number of the croup, the type of treatment (substance and/or substances injected, dose, administration route). Each animal is identified with a number from 1 to 5, written on the tail in indelible ink.

Animal weight: the mice are weighed prior to the start of treatment, and on day 5 or 7 and day 11.

The animals were treated from day 1 to day 10 with the molecules; taxol or the vehicle were administered on alternate days, on days 5, 7, 9 and 11.

The groups are: 1) blanks; 2) vehicle+PBS; 3) taxol; 4) taxol+ALC; 5) ALC; 6) ALC+vehicle. The animals are sacrificed 6 hours after the last taxol injection.

Blood and bone marrow samples are taken 6 hours after the last treatment with taxol or vehicle. The mice are anaesthetised with $CO_2$; blood is taken from the retro-orbital plexus (0.5 ml blood/mouse) and placed in Eppendorf test tubes containing 10 µl of Vister heparin (5000 U/ml). The animals are sacrificed by cervical dislocation. Later, the bone marrow samples are taken.

One blood sample and one bone marrow sample per mouse are taken at various times.

Blood Cell Count

Before starting the WBC (White Blood Cells) count, the instrument is checked by measuring the EMACHECK blood sample parameters (human check) supplied by Delcon.

The instrument is used according to the instructions provided in the operating manual. The blood (25 µl) is taken from the dilutor and brought to a volume of 10 ml with isotonic solution (PLTA Saline, Delcon) in a beaker (dil. 1:400) (Solution A). From Solution A, the dilutor takes 100 µl and brings them to 10 ml (dil. 1:100) in another beaker (Solution B). To Solution A are added 3 drops of lysing agent (Emosol, Delcon), the solution is mixed by hand and left to act for approximately 2 minutes so that the red blood cells are lysed and HGB (haemoglobin) released. Solution A containing the lysing agent is used for the WBC and haemoglobin (HGB) readings. Solution B is used for the RBC and platelet (PLT) readings.

Double readings are done on each sample, and between one sample and the next, the instrument is washed using isotonic solution, Superfrost plus slides (25×75×1 mm) (Mensel-Glaser), ready for use, are adopted. The blood (8 µl) is deposited on the right-hand side of the slide; another slide, placed at a 45° angle, to the left of the blood, is drawn back until in comes into contact with the drop which spreads rapidly along the contact line between the two slides; the slide is moved forwards with a smooth, rapid movement so as to obtain a thin film of blood. The slide is left to dry in air, stained with Diff-Quick (DADE) dye, according to the attached instructions, and dried again in air.

The slides are immersed in Histolemon solution (Carlo Erba) for 2 sec.; a drop of synthetic mountant (Shandon) os deposited at the centre of the slide and a cover slide is placed over it covering the entire blood smear, taking care not to form bubbles between the two slides. The slides are dried and then the WBC count is performed, up to 100, with an optical microscope, after depositing a drop of cedar oil on the slide.

The quantity of WBC/ml, assessed using the haemocytometer, is multiplied by the percentage value of the corresponding neutrophil granulocytes of the leukocyte formula. This parameter, divided by 100, expresses the value of neutrophils/$mm^3$ blood.

The following are regarded as normal parameter values: for WBC, counted on the haemocytometer, values of up to 18000/$mm^3$; for percentage neutrophils, counted on the slide, values of up to 18%; for absolute neutrophils calculated, values of up to 1800.

Data are expressed as means ±SE. Comparison between the neutrophil granulocyte values obtained for the different groups is done using ANOVA. Abnormal values are subjected to the Dixon test.

Taxol treatment (30 mg/kg i.p. every 2 days for a total of 4 times) caused significant neutropenia 6 hours after the last injection of the agent (−90% neutrophylic granulocytes compared to blanks, p<0.001). The oral or subcutaneous administration of acetyl L-carnitine (100 mg/kg) was found to protect the polymorphonucleates against taxol-induced damage 8–43% sc; −23% os) (Table 4).

In another experiment, the combination of ALC+taxol caused a 73% reduction in neutrophils, as against the 98% reduction obtained after administration of taxol alone. The administration of ALC or of vehicle+ALC caused no changes in neutrophils as compared to the vehicle alone or to untreated animals (blanks) (Table 4).

Three days after the last administration of taxol, neutrophil granulocytes began to recover (−64% vs vehicle), but the effect is even more marked following combined treatment with ALC+taxol (−26% vs vehicle). In this case, too, the administration of ALC or of vehicle+ALC caused no changes in neutrophils as compared to vehicle alone or untreated animals (blanks) (Table 5).

Taxol, administered 4 times on alternate days, induces severe neutropenia. The oral administration of ALC is capable of affording significant protection against the damaging effect of taxol.

EXAMPLE 6

Effect of Administration of Acetyl L-carnitine (ALC) in Combination with Taxol i.v. on Neutropenia in the Mouse Essentially, example 5 was repeated, except for the taxol administration route, which in this case was intravenous, that is to say in the actual clinical application conditions.

The experimental schedules and measurements were the same as those described in the previous example.

The results are given in Tables 6 and 7.

TABLE 4

Effect of ALC on taxol-induced neutropenia in BALB/c mice
SACRIFICE 6 HOURS AFTER LAST TAXOL ADMINISTRATION

| Group | N. | WBC $Mm^3$ | Lymphocytes % | Neutrophils % | Absolute neutrophils/$mm^3$ |
|---|---|---|---|---|---|
| Blanks | 9 | 5389 ± 362 | 88.8± 1.0 | 11.1± 1.0 | 574 ± 37 |
| Vehicle + PBS | 7 | 7107 ± 743 | 88.8± 0.9 | 11.1± 0.9 | 769 ± 83 |
| Taxol | 8 | 6781 ± 474 | 99.7± 0.1 | 0.2± 0.1 | ****13 ± 8.7 |
| Taxol + ALC | 10 | 4700 ± 443 | 95.2± 0.6 | 4.7± 0.6 | ***211° ± 29 |
| ALC | 10 | 6452 ± 270 | 88.7± 0.8 | 11.2± 0.7 | 708 ± 32 |
| Vehicle + ALC | 10 | 5950 ± 551 | 91.5± 1.1 | 8.5± 1.1 | 511 ± 92 |

Data are means ± SE.
****$P < 0.0001$ vs vehicle;
°°$P < 0.05$ vs taxol (ANOVA).

TABLE 5

Effect of ALC on taxol-induced neutropenia in BALB/c mice
SACRIFICE 3 DAYS AFTER LAST TAXOL ADMINISTRATION

| Group | N | WBC $Mm^3$ | Lymphocytes % | Neutrophils % | Absolute neutrophils/$mm^3$ |
|---|---|---|---|---|---|
| Vehicle + PBS | 10 | 4945 ± 284 | 85.9± 0.9 | 14.1 ± 0.9 | 688 ± 47 |
| Taxol | 10 | 5855 ± 520 | 95.5± 0.5 | 4.5 ± 0.5 | ****250 ± 22 |
| Taxol + ALC | 9 | 5661 ± 254 | 90.7± 0.9 | 9.3 ± 0.9 | **511°°° ± 51 |
| ALC | 10 | 6920 ± 368 | 89.9± 0.7 | 10.1 ± 0.7 | 691 ± 50 |
| Vehicle + ALC | 9 | 6067 ± 446 | 89.2± 0.9 | 10.7 ± 0.9 | 625 ± 29 |

Data are means ± SE.
****$P < 0.0001$;
**$P < 0.01$ vs vehicle;
°°°$P < 0.01$ vs taxol (ANOVA).

TABLE 6

Effect of ALC on taxol-induced neutropenia in BALB/c mice
SACRIFICE 6 HOURS AFTER FOURTH TAXOL ADMINISTRATION

| Group | N | WBC $Mm^3$ | Lymphocytes % | Neutrophils % | Absolute neutrophils/$mm^3$ |
|---|---|---|---|---|---|
| Vehicle | 10 | 6400 ± 701 | 92.7± 0.5 | 7.3± 0.5 | 471 ± 69 |
| Taxol + ALC | 8 | 6769 ± 497 | 88.4± 0.8 | °°°°11.6± 0.8 | 770°°°° ± 45 |

TABLE 6-continued

Effect of ALC on taxol-induced neutropenia in BALB/c mice
SACRIFICE 6 HOURS AFTER FOURTH TAXOL ADMINISTRATION

| Group | N | WBC Mm$^3$ | Lymphocytes % | Neutrophils % | Absolute neutrophils/mm$^3$ |
|---|---|---|---|---|---|
| Taxol | 10 | 8150 ± 683 | 97.1± 0.4 | **2.9± 0.4 | 229 ± 34 |

Data are means ± SE.
****P < 0.0001 and P < 0.01 vs vehicle;
°°°°P < 0.0001 vs taxol (ANOVA).

TABLE 7

Effect of ALC on taxol-induced neutropenia in BALB/c mice
SACRIFICE AFTER 3 DAYS' RECOVERY FROM LAST TAXOL
ADMINISTRATION (54 mg/kg/15 ml)

| Group | N | WBC mm$^3$ | Lymphocytes % | Neutrophils % | Absolute neutrophils/mm$^3$ |
|---|---|---|---|---|---|
| Vehicle | 9 | 5817 ± 512 | 91.6± 0.9 | 8.4± 0.9 | 477 ± 69 |
| Taxol + ALC | 9 | 5089 ± 480 | 92.0± 1.2 | 8.0± 1.2 | 431 ± 90 |
| Taxol | 9 | 4572 ± 290 | 93.0± 1.1 | 7.0± 1.1 | 330 ± 57 |
| Blanks | 8 | 9688 ± 497 | 92.1± 0.4 | 7.9± 0.4 | 758 ± 43 |

Data are means ± SE.
****P < 0.0001 and P < 0.01 vs vehicle;
°°°P < 0.0001 vs taxol (ANOVA).

These results confirm the protective effect of orally administered ALC.

EXAMPLE 7

Effect of Administration of Acetyl L-carnitine (ALC) in Combination with Taxol on Neutropenia in Mice with L-MM3 Carcinoma of the Breast and Evaluation of Anticancer Action In a study conducted according to Good Laboratory Practice (GLP), to evaluate the action of acetyl L-carnitine (ALC) in combination with taxol on tumour growth, Balb/c mice were inoculated with murine cancer of the breast (L-MM3) and the animals were treated both with ALC plus taxol, and with taxol or ALC alone. In addition, in this tumour model, the amount of circulating neutrophils was measured.

Acetyl L-carnitine inner salt (sterile ampoule), solubilised in water for injectable preparations, was used. Each ampoule of ALC is dissolved in 4 ml of water for injections (Solution O). 0.8 ml of (O) are brought to 50 ml with sterile PBS (Sigma) in order to perform the oral administration (100 mg/kg/50 ml).

Taxol (paclitaxel (INDENA)) is weighed, solubilised in the previously prepared specific vehicle (Cremophor® EL (BASF), diluted 1:1 with ethanol) and stored at +4° C. sheltered from the light. At the time of use, the 12 mg/ml solution is diluted 1:4 with saline in phosphate buffer (PBS) (SIGMA,) and injected i.p. (30 mg/kg/10 ml).

The essential experimental indications are given here below:

Animals: 120 female BALB/c mice weighing 18–20 g (Harlan)
Animal house conditions: 5 mice per cage; temperature 22±2° C.; relative humidity 55±15%; air changes 15–20/h; 12 h light/darkness cycle (7.00 a.m.–7.00 p.m. light); makrolon cages (26.7×20.7×14 cm) with stainless steel grilled covers; dedusted, sterile, corn-cob shaving litters.
Diet: 4RF21 feed (company: Mucedola), food and water available "ad libitum".

The randomisation is casual in blocks of animals, i.e. the animal house attendant transfers the mice from the boxes to the cages, completing one cage at a time. In a second phase, the attendant provisionally identifies all the mice, weighs them, and, if the weights present significant differences between groups, moves the animals from one cage to another, keeping the number of animals per cage unchanged. Each cage is labelled with a card bearing the number of the group, the type of treatment (substance and/or substances injected, dose, administration route). Each animal is identified with a number from 1 to 5, written on the tail in indelible ink.

Animal weight: the mice are weighed prior to the start of treatment, and on the day of the last taxol injection.

Treatment schedule 1: the transplantable murine breast cancer cells (L-MM3) of Balb/c origin are grown at 37° C. in plastic flasks in a 5% CO$_2$ humidified incubator in DMEM medium containing 5% heat-inactivated FCS, L-glutamine 2 mM, and gentamicin 80 μg/ml. At the time of inoculation, the cells are detached with trypsin-EDTA and re-suspended in the same medium without PBS.

Unanaesthetised female Balb/c mice received subcutaneous injections in the flank of 4×10$^5$ cells in 0.2 ml of DMEM.

Four days after inoculation of the tumour, the animals were treated with the molecules according to the following schedule, for the purposes of evaluating neutropenia:

| Day 1 | Day 4 | Day 8 | Day 10 | Day 12 | Day 14 |
|---|---|---|---|---|---|
| tumour inoculation | ALC→→→→→→→→→→→→→→→→→ | Tax | Tax | Tax | Tax |
| | | | | | ↓ Sacrifice after 6 h |

ALC is administered then for 10 days; the animals are sacrificed after 6 hours.

The experimental groups, each consisting of 15 mice, are:

| Group | Cage No. |
|---|---|
| Tumour + Vehicle | 1, 2, 3 |
| Tumour + Taxol + ALC | 4, 5, 6 |
| Tumour + Taxol | 7, 8, 9 |
| Tumour + Vehicle + ALC | 10, 11, 12 |

Treatment schedule 2: the same experimental groups mentioned above, each consisting of 15 mice (with different cage numbers) are treated as follows in order to evaluate survival and tumour size.

| Day 1 | Day 4 | Day 8 | Day 10 | Day 12 | Day 14 | Day 17 |
|---|---|---|---|---|---|---|
| | ↓ | ↓ | ↓ | ↓ | ↓ | ↓ |
| tumour inoculation | Tax ALC→→→→→→→→→→→→→→→→→→ | Tax | Tax | Tax | Tax | |

ALC administration lasts 14 days (in groups 16, 17, 18) and the tumour is measured until it reaches a size of approximately 2 cm. The animals are left alive for 100 days.

The experimental groups, each consisting of 15 mice, are:

| Group | Cage No |
|---|---|
| Tumour + Vehicle | 13, 14, 15 |
| Tumour + Taxol − ALC | 16, 17, 18 |
| Tumour + Taxol | 19, 20, 21 |
| Tumour + Vehicle − ALC | 22, 23, 24 |

Table of treatments and sacrifices

| Day | Cage |
|---|---|
| 1 | Inoculation: 1, 4, 7, 10, 13, 16, 19, 22 |
| 2 | Inoculation: 2, 5, 8, 11, 14, 17, 20, 23 |
| 3 | Inoculation: 3, 6, 9, 12, 15, 18, 21, 24 |
| 4 | ALC: 4, 16, 10, 22 |
| 5 | ALC: 4, 5, 16, 17, 10, 22, 11, 23 |
| 6 | ALC: 4, 5, 6, 16, 17, 18, 10, 22, 11, 23, 12, 24 |
| 7 | ALC: 4, 5, 6, 16, 17, 18, 10, 22, 11, 23, 12, 24 |
| 8 | ALC: 4, 5, 6, 16, 17, 18, 10, 22, 11, 23, 12, 24 |
| | Vehicle: 1, 13, 10, 22 |
| | Taxol: 4, 7, 16, 19 |
| 9 | ALC: 4, 5, 6, 16, 17, 18, 10, 22, 11, 23, 12, 24 |
| | Vehicle: 2, 14, 11, 23 |
| | Taxol: 5, 8, 17, 20 |

Table of treatments and sacrifices (continued)

| Day | Cage |
|---|---|
| 10 | ALC: 4, 5, 6, 16, 17, 18, 10, 22, 11, 23, 12, 24 |
| | Vehicle: 1, 3, 13, 15, 10, 22, 12, 24 |
| | Taxol: 4, 6, 7, 9, 16, 18, 19, 21 |
| 11 | ALC: 4, 5, 6, 16, 17, 18, 10, 22, 11, 23, 12, 24 |
| | Vehicle: 2, 14, 11, 23 |
| | Taxol: 5, 8, 17, 20 |
| 12 | ALC: 4, 5, 6, 16, 17, 18, 10, 22, 11, 23, 12, 24 |
| | Vehicle: 1, 3, 13, 15, 10, 22, 12, 24 |
| | Taxol: 4, 6, 7, 9, 16, 18, 19, 21 |
| 13 | ALC: 4, 5, 6, 16, 17, 18, 10, 22, 11, 23, 12, 24 |
| | Vehicle: 2, 14, 11, 23 |
| | Taxol: 5, 8, 17, 20 |
| 14 | ALC: 5, 6, 17, 18, 11, 23, 12, 24, 16, 22 |
| | Vehicle: 1, 3, 13, 15, 10, 22, 12, 24 |
| | Taxol: 4, 6, 7, 9, 16, 18, 19, 21 |
| | Sacrifice 6 h after last taxol administration in: |
| | 1. 4. 7. 10 + 3 blank animals |
| 15 | ALC: 6, 18, 12, 24, 16, 22, 17, 23 |
| | Vehicle: 2, 14, 11, 23 |
| | Taxol: 5, 8, 17, 20 |
| | Sacrifice 6 h after last taxol injection in: |
| | 2. 5. 8. 11 + 3 blank animals |
| 16 | ALC: 16, 22, 17, 23, 18, 24 |
| | Taxol: 6, 9, 18, 21 |
| | Vehicle: 3, 15, 12, 24 |
| | Sacrifice 6 h after last taxol injection in: |
| | 3. 6. 9. 12 + 4 blank animals |
| 17 | ALC: 16, 22, 17, 23, 18, 24 |
| 18 | ALC: 17, 23, 18, 24 |
| 19 | ALC: 18, 24 |

The tumour size (length and width) is measured twice a week with a calliper, from the tumour is measurable. Tumour size is expressed in cm and is evaluated according to the following formula: $\sqrt{(\text{length} \times \text{width})}$.

Tumour measurement schedule

| Day after inoculation | Cage (comprising 5 mice) |
|---|---|
| 22 | 13, 16, 19, 22 |
| | 14, 17, 20, 23 |
| | 15, 18, 21, 24 |
| 23 | 13, 16, 19, 22 |
| | 14, 17, 20, 23 |
| | 15, 18, 21, 24 |
| 28 | 13, 16, 19, 22 |
| | 14, 17, 20, 23 |
| | 15, 18, 21, 24 |
| 30 | 13, 16, 19, 22 |
| | 14, 17, 20, 23 |
| | 15, 18, 21, 24 |
| 35 | 13, 16, 19, 22 |
| | 14, 17, 20, 23 |
| | 15, 18, 21, 24 |
| 36 | 13, 16, 19, 22 |
| | 14, 17, 20, 23 |
| | 15, 18, 21, 24 |

-continued

Tumour measurement schedule

| Day after inoculation | Cage (comprising 5 mice) |
|---|---|
| 42 | 13, 16, 19, 22 |
|  | 14, 17, 20, 23 |
|  | 15, 18, 21, 24 |
| 44 | 13, 16, 19, 22 |
|  | 14, 17, 20, 23 |
|  | 15, 18, 21, 24 |
| 49 | 13, 16, 19, 22 |
|  | 14, 17, 20, 23 |
|  | 15, 18, 21, 24 |

Blood and bone marrow samples are taken for the first treatment schedule animals. On the days they are sacrificed, the mice are anaesthetised with $CO_2$; blood is taken from the retro-orbital plexus (0.5 ml blood/mouse) and placed in Eppendorf test tubes containing 10 μl of Vister heparin (5000 U/ml). The animals are sacrificed by cervical dislocation. Later, the bone marrow samples are taken.

One blood sample and one bone marrow sample per mouse are taken at various times.

Blood Cell Count

Before starting the WBC count, the instrument is checked by measuring the EMACHECK blood sample parameters (human check) supplied by Delcon.

The instrument is used according to the instructions provided in the operating manual. The blood (25 μl) is taken from the dilutor and brought to a volume of 10 ml with isotonic solution (PLTA Saline, Delcon) in a beaker (dil. 1:400) (Solution A). From Solution A, the dilutor takes 100 μl and brings them to 10 ml (dil. 1:100) in another beaker (Solution B). To Solution A are added 3 drops of lysing agent (Emosol, Delcon), the solution is mixed by hand and left to act for approximately 2 minutes so that the red blood cells are lysed and HGB (haemoglobin) released. Solution A containing the lysing agent is used for the WBC and haemoglobin (HGB) readings. Solution B is used for the RBC and platelet (PLT) readings.

Double readings are done on each sample, and between one sample and the next, the instrument is washed using isotonic solution, Superfrost plus slides (25×75×1 mm) (Mensel-Glaser), ready for use, are adopted. The blood (8 μl) is deposited on the right-hand side of the slide; another slide, placed at a 45° angle, to the left of the blood, is drawn back until in comes into contact with the drop which spreads rapidly along the contact line between the two slides; the slide is moved forwards with a smooth, rapid movement so as to obtain a thin film of blood. The slide is left to dry in air, stained with Diff-Quick (DADE) dye, according to the attached instructions, and dried again in air.

The slides are immersed in Histolemon solution (Carlo Erba) for 2 sec.; a drop of synthetic mountant (Shandon) is deposited at the centre of the slide and a cover slide is placed over it covering the entire blood smear, taking care not to form bubbles between the two slides. The slides are dried and then the WBC count is performed, up to 100, with an optical microscope, after depositing a drop of cedar oil on the slide.

The quantity of WBC/ml, assessed using the haemocytometer, is multiplied by the percentage value of the corresponding neutrophil granulocytes of the leukocyte formula. This parameter, divided by 100, expresses the value of neutrophils/mm$^3$ blood.

Comparison between the neutrophil granulocyte values obtained for the different groups is done using ANOVA. Tumour sizes are compared using the non-parametric Mann Whitney test for unpaired data.

Taxol treatment (30 mg/kg i.p. every 2 days for a total of 4 times) caused a significant reduction in polymorphonucleates (−93%, vs vehicle, p<0.0001) in the mouse inoculated with L-MM3 murine breast cancer. The oral administration of acetyl L-carnitine (100 mg/kg once daily for 10 days) combined with treatment with taxol proved capable of significantly counteracting the taxol-induced reduction in neutrophil granulocytes (335/mm$^3$ vs 65/mm$^3$, °°p<0.01) (Table 8).

Taxol, injected according to the same schedule used for evaluation of neutrophil granulocytes (30 mg/kg i.p. every two days for a total of 4 times), was found to significantly inhibit L-MM3 tumour growth, which was monitored until the tumour size reached approximately 2 cm in the control group (0.56 cm vs 1.8 cm, p<0.0001). Combined treatment with orally administered ALC for 14 days (100 mg/kg once daily) plus taxol (30 mg/kg i.p. every 2 days for a total of 4 times) did not affect the anticancer activity of taxol.

In conclusion, in this tumour model, too, taxol caused severe neutropenia and ALC, administered continuously over the period in which this type of bone marrow toxicity occurs, was capable of preventing the taxol-induced reduction in polymorphonucleates. At the same time, the action of ALC did not affect the anticancer activity of taxol.

TABLE 8

Effect of ALC on taxol-induced neutropenia in BALB/c mice inoculated with murine carcinoma of the breast (L-MM3)
SACRIFICE 6 HOURS AFTER LAST TAXOL ADMINISTRATION

| Group | N | WBC Mm$^3$ | Lymphocytes % | Neutrophils % | Absolute neutrophils/mm$^3$ | Platelets mm$^3$ |
|---|---|---|---|---|---|---|
| Vehicle | 10 | 7600 ± 729 | 86.8 ± 1.1 | 13.2 ± 1.1 | 965 ± 110 | 402600 ± 22727 |
| Tax + ALC | 15 | 5820 ± 250 | 94 ± 0.8 | ***5.9°°° ± 0.8 | ****335°° ± 45 | 502733 ± 27474 |
| Taxol | 13 | 4600 ± 242 | 98.6 ± 0.2 | ****1.3 ± 0.2 | ****65 ± 14 | 539000 ± 36057 |
| Vehicle + ALC | 12 | 4950 ± 385 | 87.6 ± 0.9 | 12.3 ± 0.9 | ***607 ± 68 | 433000 ± 45731 |

Data are means ± SE. **P < 0.0001; *P < 0.001 vs vehicle; °°P < 0.01; °°°P < 0.001 vs taxol (ANOVA).

Evaluation of the Effect of Acetyl L-carnitine (ALC) on the Anticancer Action of Taxol in M109 Murine Lung Cancer Taxol has proved effective in the treatment of cancer of the ovaries, breast and lungs and in other types of cancers (Rowinsky, E. K., and R. C. Donehower, (1991); Pharmacol. Ther. 52:35.). The anticancer action of this compound is related mainly to its ability to inhibit depolymerisation of the microtubules in tubulin monomers (Schiff, P. B., J. Fant, and S. B. Horwitz. 1979. Nature); this effect blocks the proliferating cells in the $G_2/M$ phase of the cell cycle, i.e. between the last stage of the interphase in which DNA synthesis is completed and the subsequent period of cell division or mitosis, and this leads, in the cell, to the start of a cascade of events typical of the apoptotic process. Taxol, like other chemotherapeutic agents, moreover, is associated with side effects such as neuropathies and myelosuppression.

On comparing the statistical data obtained in the groups of animals treated with vehicle alone and those treated with taxol in combination with orally administered acetyl L-carnitine, a statistically significant reduction of the tumour mass was found in the latter at all observation times. By contrast, comparison of the group treated with vehicle alone and the one treated with vehicle in combination with administration of acetyl L-carnitine revealed no statistically significant differences in tumour mass growth at any of the observation times. Analysis of the data relating to the comparison between the group treated with taxol and the one treated with taxol in combination with acetyl L-carnitine showed no significant differences in tumour weight. As regards the analysis of the number of metastases, the data obtained show a statistically significant reduction in that number in the groups treated with taxol, with taxol in combination with acetyl L-carnitine and with vehicle in combination with acetyl L-carnitine as compared to the group treated with vehicle alone. In particular, the mice treated with taxol or with taxol in combination with acetyl L-carnitine also showed a reduction in the diameter of the metastases compared to the groups treated with vehicle alone or with vehicle in combination with acetyl L-carnitine. On the basis of analysis of the following data, we can therefore state that acetyl L-carnitine does not interfere with the anticancer action of taxol in terms of inhibition of the tumour mass. In addition, acetyl L-carnitine showed a significant inhibitory effect on the formation of lung metastases.

The following example illustrates this further aspect of the invention.

EXAMPLE 8

Evaluation of the Effect of Acetyl L-carnitine (ALC) on the Anticancer Action of Taxol in Mice with M109 Lung Cancer In a study conducted according to Good Laboratory Practice (GLP), to evaluate the action of acetyl L-carnitine (ALC) in combination with taxol on tumour growth, Balb/c mice were inoculated with murine lung cancer (M109) and the animals were treated both with ALC plus taxol and with taxol or ALC alone. In addition, in this tumour model, the amount of circulating neutrophils was measured.

Acetyl L-carnitine inner salt (sterile ampoule, 0.5 g), solubilised in water for injectable preparations, was used.

Each ampoule of ALC is dissolved in 4 ml of the solvent provided (solution O). To be precise, 1.6 ml of solution O are brought to 40 ml with sterile buffer solution (PBS, Sigma P-4417) and then administered orally (100 mg/kg/20 ml).

Taxol (paclitaxel (INDENA), cod. 3926570) is weighed, solubilised in the specific vehicle (Cremophor® EL (BASF), diluted 1:1 with ethanol) and stored at +4° C., sheltered from the light. At the time of use, the 12 mg/ml solution is diluted 1:4 with saline in phosphate buffer (PBS) (SIGMA,) and injected i.p. (30 mg/kg/ 10 ml).

Animals: 60 female Balb/c mice weighing 18 g (Harlan).

Animal house conditions: 5 mice per cage; temperature 22±2° C.; relative humidity 55±15%; air changes 15–20/h; 12 h light/darkness cycle (7.00 a.m.–7.00 p.m. light); makrolon cages (26.7×20.7×14 cm) with stainless steel grilled covers; dedusted, sterile, corn-cob shaving litters.

Diet: 4RF21 feed (company: Mucedola), food and water available "ad libitum".

Randomisation: casual in blocks of animals.

Animal weight: the mice are weighed prior to the start of treatment and then once a week up to the end of the experiment.

M109 tumour cells isolated from solid tumour.

The procedure described by Kedar E., B. Ikejiri, G. D. Bannard and R. B. Herberman (Eur. J. Cancer Clin. Oncol. 18; 991: 1982) is adopted with modifications. One Balb/c mouse (donor) was sacrificed by cervical dislocation, and after washing its back with denatured alcohol, the dorsal skin was cut longitudinally into two flaps which were detached to remove the tumour mass. The latter was placed on sterile gauze, where it was freed of connective tissue adhesions and of the necrotic and haemorrhagic parts. The study tissue was placed in a plate containing PBS with $Ca^{++}$ and $Mg^{++}$ (Gibco) at pH 7.2 and cold, broken down into pieces measuring 2–3 mm and re-suspended in a solution (15 ml solution/g tumour) of PBS with $Ca^{++}$ and $Mg^{++}$, pH 7.2m containing 2 mg/ml trypsin (type III. 10000 U/mg protein, Sigma-Aldrich), 2 mg/ml collagenase (type I-S 180 U/mg solid, Sigma), 0.2 mg/ml DNAse (type I 1548 U/mg protein. Sigma) and 25 µg/ml gentamicin (Sigma) and incubated at 37° C. for 15 minutes under constant stirring. The cell suspension was then homogenised with the aid of a potter (B. Braun) for 2 minutes, incubated at 37° C. for 10 minutes and aspirated gently a number of times with a syringe with a No. 21 sterile needle. After addition of 30 ml of RPMI-1640 (Eurobio) containing 10% FBS (Eurobio) maintained at 4° C. the cell suspension was filtered on sterile gauze and then centrifuged at 700 g for 10 minutes. The cell pellet was re-suspended gently in RPMI-1640 containing 10% FBS and 0.2 mg/ml DNAse (Sigma) and then centrifuged at 700 g for 10 minutes. The pellet was consecutively subjected to two washings with RPMI-1640; at the end of the last washing, the pellet was re-suspended gently in RPMI-1640 so as to perform the count to establish the cell concentration.

Cell count under the microscope: the cell count is performed by means of the Trypan-Blue vital stain exclusion test; the tumour cells are suitably diluted with 0.4% Trypan-Blue (Sigma), a vital stain, which makes it possible to distinguish between viable and dead cells. The dilution containing the cells to be counted was stirred gently, 10 µl were removed and used to set up a Burker chamber. A square grid delimited by the three triple lines was used, comprising 16 small squares (4×4) delimited from one another by double lines. Both viable cells (which have a translucid appearance) and dead cells (which are blue in appearance, having incorporated the stain) which are to be found positioned inside the square formed by the median line and the triple lines, or on the line itself. This operation was repeated for another three squares, after which the sum of the cells counted in each square was calculated and the arithmetic mean was determined for the readings taken in the four squares. The arithmetic mean of the viable cells was multiplied by the dilution factor used and by the specific power factor for the type of chamber used for the count ($10^4$), thus obtaining the number of viable cells contained in one milliliter. The ratio of the arithmetic mean of the viable cells to the arithmetic mean of total cells, multiplied by a hundred, expresses the percentage cell viability.

Inoculation conditions: 60 unanaesthetised Balb/c mice weighing approximately 18 g (Harlan) received i.m. injections of $3\times10^5$ M109 lung cancer cells in 0.1 ml of RPMI-1640 (Sigma) in the right rear paw.

Treatment schedule: for the purposes of evaluating tumour size in the experimental study groups, each consisting of 15 Balb/c mice, $3\times10^5$ M109 lung cancer cells were inoculated, and the study molecules were administered at the scheduled times. ALC was administered at the dose of 100 mg/kg (os) from day 4 to day 17. The vehicle diluted 1:4 with PBS from the mother solution was administered i.p. on days 8, 10, 12 and 14. Taxol was administered at the dose of 30 mg/kg (i.p.) on days 8, 10, 12 and 14, described in the following schedule:

| Day 1 | Day 4 | Day 8 | Day 10 | Day 12 | Day 14 | Day 17 |
|---|---|---|---|---|---|---|
| tumour inoculation | ALC → | Tax →→→ | Tax →→→ | Tax →→→ | Tax →→→ | →→ |

The animals were kept under observation up to day 22 after inoculation of the M109 murine lung cancer cells, and were then sacrificed the lungs removed to determine the number of metastases.

The experimental groups, each comprising 15 mice, are:

| Group | Cage No |
|---|---|
| Tumour + Vehicle + ALC | 1, 2, 3 |
| Tumour + Taxol + ALC | 4, 5, 6 |
| Tumour + Taxol | 7, 8, 9 |
| Tumour + Vehicle | 10, 11, 12 |

| Treatment table: | | |
|---|---|---|
| DAY | TREATMENT | CAGE No |
| 1 | Cell inoculation | 1,2,3,4,5,6,7,8,9,10,11,12, |
| 2 | ALC | 1,2,3,4,5,6 |
| 3 | ALC | 1,2,3,4,5,6 |
| 4 | ALC | 1,2,3,4,5,6 |
| 5 | ALC | 1,2,3,4,5,6 |
| 6 | ALC | 1,2,3,4,5,6 |
|   | TAX | 4,5,6,7,8,9 |
|   | VEHIC | 1,2,3,10,11,12, |
| 7 | ALC | 1,2,3,4,5,6 |
| 8 | ALC | 1,2,3,4,5,6 |
|   | TAX | 4,5,6,7,8,9 |
|   | VEHIC | 1,2,3,10,11,12, |
| 9 | ALC | 1,2,3,4,5,6 |
| 10 | ALC | 1,2,3,4,5,6 |
|   | TAX | 4,5,6,7,8,9 |
|   | VEHIC | 1,2,3,10,11,12, |
| 11 | ALC | 1,2,3,4,5,6 |
| 12 | ALC | 1,2,3,4,5,6 |
|   | TAX | 4,5,6,7,8,9 |
|   | VEHIC | 1,2,3,10,11,12, |
| 13 | ALC | 1,2,3,4,5,6 |
| 14 | ALC | 1,2,3,4,5,6 |
| 15 | ALC | 1,2,3,4,5,6 |

| Tumour measurement schedule: | |
|---|---|
| Day after inoc. | Cage No |
| 4 | 1,2,3,4,5,6,7,8,9,10,11,12 |
| 8 | 1,2,3,4,5,6,7,8,9,10,11,12 |
| 13 | 1,2,3,4,5,6,7,8,9,10,11,12 |
| 15 | 1,2,3,4,5,7,3,9,10,11,12 |
| 18 | 1,2,3,4,5,6,7,8,9,10,11,12 |
| 20 | 1,2,3,4,5,6,7,8,9,10,11,12 |

Tumour measurement: the tumour was measured with a calliper three times a week as soon as it became palpable. The tumour mass is calculated on the basis of the measurements of the two dimensions (length and width), expressed in mm. according to the following formula:

$$\frac{(\text{length} \times \text{width}^2)}{2} = \text{tumour volume} (\text{mm}^3).$$

If we consider conventionally a tumour density equal to 1, the result is that the tumour volume expressed in $mm^3$ is equal to the weight of the tumour expressed in mg.

Determination of the number of lung metastases: on day 22 after inoculation of M109 murine lung cancer, the study animals were sacrificed by cervical dislocation. Their lungs were then removed and kept for approximately 5–7 days in 5 ml of Bouin's solution with the following composition: 71% as saturated picric acid solution (Merck), and 24% as 10% formaldehyde (Fluka). When lung metastases were evident, their numbers were counted.

Statistical analysis of the data for tumour size and number of lung metastases was carried out using the non-parametric Mann-Whitney test for unpaired data.

Analysis of the data obtained in the various groups of study animals shows inhibition of tumour mass growth in the group of mice treated with 30 mg/kg of taxol administered i.p., as compared to the mice in the group treated with vehicle alone (Table 9). This phenomenon is already marked after only the first administration of the agent, and the difference in weight of the tumours between the group treated with taxol and the one treated with vehicle alone proved statistically significant with $p<0.01$. After the second administration, the reduction in tumour mass observed is maintained, with a statistically significant difference ($p<0.0001$) as compared to the group treated with vehicle alone, and this inhibition of the tumour mass is maintained after the following administrations. The group of animals treated with taxol administered i.p. at the dose of 30 mg/kg in combination with acetyl L-carnitine administered orally at the dose of 100 mg/kg already shows a reduction in tumour mass growth as compared to vehicle alone after the first treatment, with a significance of $p<0.05$. This trend is also maintained after the subsequent administrations. On all the days the analysis was carried out, the group treated with vehicle in combination with acetyl L-carnitine showed no highly significant difference in tumour mass growth as compared to the group treated with vehicle alone. Moreover, comparison between the group treated with taxol alone and the one receiving combined treatment with taxol plus acetyl L-carnitine revealed no statistically significant differences in tumour mass size on any of the days analysed. On the basis of analysis of the following data, we can therefore state that acetyl L-carnitine does not interfere with the anticancer action of taxol in terms of inhibition of the tumour mass.

As regards the analysis of the number of metastases at the end of the experiment, the data obtained show a statistically significant reduction in their number in the groups treated with taxol, with taxol combined with acetyl L-carnitine and with vehicle combined with acetyl L-carnitine as compared to the group treated with vehicle alone. In particular, the mice treated with taxol or with taxol combined with acetyl L-carnitine also showed a reduction in the diameter of the metastases as compared to the groups treated with vehicle alone or with vehicle plus acetyl L-carnitine (see Table 10). On the basis of analysis of the data obtained, it might be suggested that acetyl L-carnitine has a mild inhibitory effect on the formation of lung metastases.

TABLE 9

Effect of combined ALC + taxol treatment on growth of M109 murine lung cancer in BALB/c mice

| Group | Tumour size ($mm^3$ ± SEM) | | | | |
|---|---|---|---|---|---|
| | Day 8 | Day 11 | Day 13 | Day 15 | Day 20 |
| Vehicle | 563 ± 26 | 917 ± 59 | 1137 ± 50 | 1583 ± 62 | 2305 ± 146 |
| Vehicle + ALC | 567 ± 33 | 959 ± 50 | 1289 ± 39 | 1779* ± 57 | 2251 ± 78 |
| Taxol | 539 ± 43 | 662** ± 50 | 622**** ± 47 | 857**** ± 70 | 1085**** ± 116 |
| Taxol + ALC | 585 ± 25 | 716* ± 51 | 714*** ± 61 | 919**** ± 63 | 1202**** ± 72 |

Female BALB/c mice weighing approximately 20 g received i.m. injections of M109 murine lung cancer (3 × $10^5$ cells/mouse). The tumours were measured on the post-inoculation days indicated. Animals were treated with ALC and taxol according to the treatment schedule. Significance was assessed by comparing the various treatment groups versus the group treated with vehicle alone
*$P < 0.05$, $P < 0.01$, *$P < 0.001$, ****$P < 0.0001$
The data were analysed statistically using the Mann-Whitney test for paired data.

TABLE 10

Determination of number of lung metastases on day 22 after inoculation of M109 murine lung cancer in BALB/c mice after combined treatment with taxol + ALC.

| Group | n animals | (Mean ± SD) | Size of metastases |
|---|---|---|---|
| Vehicle | 6 | 109.3 ± 20.1 | M, S |
| ♦Vehicle + ALC | 9 | **77 ± 13.2 | M, S |
| ♦Taxol | 12 | **9 ± 7.3 | S |
| ♦Taxol + ALC | 13 | ***5 ± 2.4 | S |

Female BALB/c mice weighing approximately 20 g received i.m. injections of M109 murine lung cancer (3 × $10^5$ cells/mouse). Animals were treated with ALC and taxol according to the treatment schedule. On day 22 after inoculation of the tumour, the animals were sacrificed, their lungs were removed and stored in Bouin's solution. The number of metastases was evaluated 10 days after taking the samples.
♦Significance was assessed by comparing the various treatment groups versus the group treated with vehicle alone *$P < 0.05$ vs vehicle, $P < 0.01$, *$P < 0.001$.
Taxol vs taxol + ALC was significant ($P < 0.05$).
The data were analysed statistically using the Mann-Whitney test for paired data.
M = Medium (1–2 mm diam); S = Small (<1 mm diam).

ALC does not interfere with the therapeutic effect of taxol, and this aspect has also been evaluated in a human tumour model, as illustrated in the following example.

EXAMPLE 9

Study of the Influence of Acetyl L-carnitine (ALC) Treatment on the Anticancer Activity of Taxol in a Human Tumour Model Cell cultures of LOVO human colon cancer, transplanted in hairless mice, were used.

The tumour was inoculated in solid fragments in both flanks of the mice (day 0).

The inoculated tumours were measured with a calliper and when a mean tumour weight of 100 mg was reached (day 7), the animals were divided into 4 groups of 5 animals each according to the following schedule:

| Group 1 | Controls |
|---|---|
| Group 2 | taxol |
| Group 3 | ALC |
| Group 4 | taxol + ALC |

On the same day, ALC treatment was initiated and was continued for 18 consecutive days (qdx18) (groups 3 and 4). ALC was administered at the dose of 100 mg/kg with an administration volume of 25 ml/kg.

Taxol (54 mg/kg/15 ml/kg) was administered i.v. according to a schedule consisting in a total of 4 administrations at 4-day intervals (q4dx4; days 10, 14, 18, 22) (groups 2 and 4).

In the course of the treatment and in the following three weeks at fortnightly intervals, the tumours were measured and tumour volume inhibition was calculated (TVI%, calculated as 100-(mean weight of tumours treated/mean weight of control tumours×100)) as obtained with the various treatments.

Taxol treatment caused an inhibition of tumour growth (TVI=88%). Treatment with ALC had no effect on tumour growth, which was similar to that in control group tumours. Combined treatment with taxol plus ALC showed an anticancer efficacy (TVI=90%) almost identical to that achieved with taxol alone, confirming that ALC does not interfere with the cytotoxic activity of taxol.

EXAMPLE 10

Study of the Influence of Acetyl L-carnitine (ACL) Treatment on Bleomycin-induced Pulmonary Toxicity Hamsters weighing 120 g were treated with bleomycin (1 unit) by the intratracheal route (IT) or with an equivalent volume of saline. In addition, the animals were pre-treated with ALC (200 mg/kg) or saline intraperitoneally just before the instillation of bleomycin, followed by daily injections for 1 week. The animals were allowed 3 weeks to recover prior to taking the tissue samples. At the time tissue samples were taken (day 22), one lung of each animal was prepared for histological investigation and the other lung for quantitative determination of hydroxyproline.

The experimental groups were organised as follows:
1. Pre-treatment with saline/saline IT
2. Pre-treatment with saline/bleomycin IT
3. Pre-treatment with ALC/saline IT
4. Pre-treatment with ALC/bleomycin IT Three experiments were carried out, in a total of 41 animals.

The lungs were fixed by insufflation at 20 cm of H₂O ex vivo with 10% formaldehyde in PBS (pH 7), embedded in paraffin, sectioned and stained with haematoxylin/eosin. Sections with similar orientation from the portion of the pulmonary lobe—upper, middle and lower, respectively— were examined to verify the presence and degree of inflammatory infiltrate, oedema and interstitial and intra-alveolar fibrosis.

The lungs receiving saline or pre-treatment with ALC/saline IT presented a normal alveolar architecture. The animals treated with bleomycin IT or with pre-treatment with saline alone presented dense fibrosis, alveolar atelectasis and oedema. In the animals pre-treated with ALC, there were a number of fibrotic areas, which, however, appeared thinner with less dense areas of collapse.

The hydroxyproline content (one of the main constituents of collagen) was measured using the known Woessner method. Lung samples were homogenised, hydrolysed with NaOH, and then left to oxidise before adding Erlich aldehyde reagent. Duplicate aliquots of each sample were assayed by spectrophotometry and compared with a standard calibration curve obtained with purified hydroxyproline. The hydroxyproline content (HYP) is expressed as mg/lung.

The untreated hamsters or those treated with ALC alone presented HYP levels compatible with normal accepted values. The animals treated with bleomycin presented an increase in HYP consistent with the increased deposition of collagen during the fibrotic reaction. However, the animals treated with ALC showed a reduction in HYP as compared to those treated with bleomycin, consistent with the improvement in the fibrotic response.

| Group | HYP |
|---|---|
| Saline/saline | 0.741 |
| Saline/bleomycin | 1.831 |
| ALC/saline | 0.801 |
| ALC/bleomycin | 1.380 |

ALC causes a reduction of the fibrotic response in animals treated with bleomycin.

EXAMPLE 11

Increase in the Anticancer Activity of Taxol in the Presence of Propionyl L-carnitine (PLC) In Vivo

Cell Cultures and Tumour Inoculation Conditions

Cell cultures of L-MM3 murine breast cancer cells were used, cultured at 37° C. in plastic flasks in a humidified atmosphere with 5% CO². The cells were grown in DMEM supplemented with 10% FCS and in the presence of 2 mM L-glutamine and 80 µg/ml of gentamicin. The subconfluent cells were collected during the exponential growth phase using trypsin-EDTA and re-suspended in DMEM. They were then injected subcutaneously in female Balb/c mice weighing 20 g at a density of 4×10⁵.

Tumour Measurement Method

The tumour was measured with a calliper three times a week as soon as it became palpable. The tumour mass is calculated on the basis of the measurements of the two dimensions (length and width), expressed in mm, according to the following formula:

$$\frac{(\text{length} \times \text{width}^2)}{2} = \text{tumour volume (mm}^3\text{)}.$$

If we consider conventionally a tumour density equal to 1, the result is that the tumour volume is equal to (mm³=mg).

Taxol Preparation Method

Agent used: taxol (paclitaxel INDENA). The agent is weighed, solubilised in the specific vehicle (12 mg/ml), and stored at +4° C., sheltered from the light. At the time of use, it is diluted 1:4 with saline solution in phosphate buffer (PBS, SIGMA) and injected.

Agent Vehicle: Cremophor EL (BASF)

Cremophor is diluted 1:1 with ethanol and stored sheltered from the light. On the day of treatment it is diluted 1:4 with PBS.

The animals were selected and treated as described in the previous examples.

Treatment Conditions

Schedule A). The mice were treated i.p. with 30 mg/kg of taxol and s.c. with 100 g/kg of PLC according to the following schedule.

| | Day | Treatment |
|---|---|---|
| A) | 0 | Inoculation of 400,000 cells/mouse |
| | 12 | Administration of 100 mg/kg s.c. of PLC |
| | 13 | PLC |
| | 14 | PLC |
| | 15 | PLC + Taxol (30 mg/kg) |
| | 16 | PLC |
| | 17 | PLC + Taxol |
| | 18 | PLC |
| | 19 | PLC + Taxol |
| | 20 | PLC |
| | 21 | PLC + Taxol |
| | 22 | PLC |
| | 23 | PLC |
| | 24 | PLC |
| B) | 0 | Inoculation of 400,000 cells/mouse |
| | 4 | Administration of 100 mg/kg s.c. of PLC |
| | 5 | PLC |
| | 6 | PLC |
| | 7 | PLC |
| | 8 | PLC + Taxol 30 mg/kg i.p. |
| | 9 | PLC |
| | 10 | PLC + Taxol |
| | 11 | PLC |
| | 12 | PLC + Taxol |
| | 13 | PLC |
| | 14 | PLC + Taxol |
| | 15 | PLC |
| | ↓ | |
| | 59 | PLC |

In both treatment schedules, the control, taxol and PLC groups were inoculated with the same number of cells.

In addition, the taxol treatment was given according to the same procedures and at the same times both in the group treated with taxol alone and in the one treated with taxol and PLC.

Treatment with PLC, whether alone or in combination with taxol, in treatment schedule A) starts on day 12/after inoculation of the tumour) and ends on day 24; in treatment schedule B), the treatment starts on day 5 after inoculation of the tumour and ends at the end of the experiment, i.e. on day 59.

RESULTS

Experiment A

| | Animals with tumours/total number of animals | | | |
|---|---|---|---|---|
| Day | Control | Taxol | Taxol + PLC | PLC |
| 19 | 8/13 | 6/13 | 4/12 | 4/12 |
| 22 | 10/13 | 6/13 | 6/12 | 6/12 |
| 25 | 11/13 | 7/13 | 6/12 | 9/12 |
| 28 | 12/13 | 9/13 | 6/12 | 11/12 |
| 36 | 13/13 | 11/13 | 7/12 | 12/12 |
| 46 | 13/13 | 11/13 | 8/12 | 12/12 |

| | Tumour size | | | |
|---|---|---|---|---|
| Day | Control SE | Taxol + PLC | Taxol + PLC | PLC |
| 0 | 0 | 0 | 0 | 0 |
| 22 | 2.30 ± 0.23 | 0.8 ± 0.4 | 0.4 ± 0.3 | 0.6 ± 0.3 |
| 25 | 3 ± 0.6 | 0.96 ± 0.4 | 0.5 ± 0.32 | 1.2 ± 0.38 |
| 28 | 3.9 ± 0.6 | 1.4 ± 0.4 | 0.8 ± 0.52 | 3 ± 0.4 |
| 36 | 9.5 ± 0.6 | 5.5 ± 0.5 | 3.4 ± 1.25 | 9.5 ± 0.8 |
| 46 | 14.3 ± 0.86 | 11 ± 1.5 | 7.6 ± 2.15 | 15 ± 1.1 |

On applying the non-parametric Mann-Whitney test for unpaired data, significant differences were found at all observation times in the taxol+PLC group versus the control group, with p<0.003, and only at the last observation time (day 46) did the significance level drop to p<0.034. It should be noted that the values for the taxol group on day 46 were not significantly different from the control group values.

Experiment B

| | Animals with tumours/total animals | | | |
|---|---|---|---|---|
| Day | Control | Taxol | Taxol + PLC | PLC |
| 31 | 4/11 | 2/10 | 1/10 | 3/10 |
| 45 | 8/11 | 5/10 | 4/10 | 8/10 |
| 59 | 10/11 | 6/10 | 6/10 | 8/10 |

| | Tumour size | | | |
|---|---|---|---|---|
| Day | Control | Taxol | Taxol + PLC | PLC |
| 0 | 0 | 0 | 0 | 0 |
| 26 | 0.4 ± 0.2 | 0.1 ± 0.6 | 000 | 0.4 ± 0.3 |
| 31 | 0.6 ± 0.3 | 0.2 ± 0.2 | 000 | 0.5 ± 0.3 |
| 37 | 1.9 ± 0.8 | 0.45 ± 0.2 | 0.050 ± 0.050 | 1.3 ± 0.6 |
| 41 | 3.1 ± 1.3 | 1.750 ± 1.1 | 0.1 ± 0.060 | 2.2 ± 1.0 |
| 45 | 3.59 ± 1.3 | 2.250 ± 1.130 | 0.4 ± 0.2 | 3.9 ± 1.2 |
| 53 | 7.2 ± 2 | 5.000 ± 2.2 | 2 ± 0.8 | 5.6 ± 1.4 |
| 59 | 9.6 ± 1.9 | 5.6 ± 2.2 | 3.950 ± 1.5 | 8 ± 2.2 |

The Wilcoxon statistical test was applied in this experiment, which revealed that only the control group was significantly different from the Taxol+PLC group, with p<0.05.

What is claimed is:

1. A method of mitigating the side effects of anti-tumor therapy comprising the coordinated use of a therapeutically effective amount of an anticancer agent to treat tumors sensitive to said anticancer agent, wherein the anticancer agent is selected from the group consisting of taxol, carboplatin, bleomycin and vincristine, and a detoxifying amount of acetyl L-carnitine, or one of its pharmacologically acceptable salts, to reduce the toxicity induced by the anticancer agent, while at the same time conserving its anticancer efficacy.

2. The method according to claim 1, in which the pharmacologically acceptable salt is selected from the group consisting of chloride, bromide, orotate, acid aspartate, acid citrate, acid phosphate, fumarate and acid fumarate, maleate and acid maleate, acid oxalate, acid sulphate, glucose phosphate, tartrate and acid tartrate.

3. The method according to claim 1, which the administration is sequential.

4. The method according to claim 1, in which the administration of the anticancer agent and of acetyl L-carnitine is substantially simultaneous.

5. The method according to claim 1, in which the anticancer is taxol.

6. The method according to claim 1, in which the anticancer is carboplatin.

7. The method according to claim 1, in which the anticancer is bleomycin.

8. The method according to claim 1, in which the anticancer is vincristine.

\* \* \* \* \*